(12) United States Patent
Kacham (10) Patent No.: US 11,992,391 B2
(45) Date of Patent: May 28, 2024

(54) ADHESIVE BANDAGE

(71) Applicant: C4KACHAMS, LLC, Palm Beach Gardens, FL (US)

(72) Inventor: Rithika Kacham, Palm Beach Gardens, FL (US)

(*) Notice: Subject to any disclaimer, the term of this patent is extended or adjusted under 35 U.S.C. 154(b) by 127 days.

(21) Appl. No.: 16/819,027

(22) Filed: Mar. 13, 2020

(65) Prior Publication Data

US 2021/0282977 A1    Sep. 16, 2021

(51) Int. Cl.
*A61F 13/02* (2024.01)
*A61F 13/0246* (2024.01)
(Continued)

(52) U.S. Cl.
CPC ...... *A61F 13/0266* (2013.01); *A61F 13/0253* (2013.01); *A61L 15/44* (2013.01); *A61L 15/58* (2013.01)

(58) Field of Classification Search
CPC .......... A61F 13/00; A61F 13/02; A61F 13/58; A61F 13/581; A61F 13/00021; A61F 13/0266; A61F 13/0253; A61F 13/0246; A61F 13/0259; A61F 2013/00089; A61F 2013/00238; A61F 2013/00246; A61F 2013/00251; A61F 2013/00255; A61F 2013/00263; A61F 2013/00289; A61F 2013/00561; A61F 2013/00582; A61F 2013/00655; A61F 2013/00719; A61F 2013/00855; A61F 2013/00859; A61F 2013/00863; A61F 2013/00876; A61F 2013/00897; A61F 2013/00361; A61F 2013/00259; A61F 2013/60; A61F 15/001; A61F 15/004; A61L 15/44; A61L 15/58
(Continued)

(56) References Cited

U.S. PATENT DOCUMENTS

| 4,418,822 A | * | 12/1983 | Dotta | A61F 13/0203 |
| | | | | 602/57 |
| 5,242,433 A | * | 9/1993 | Smith | A61M 35/006 |
| | | | | 600/556 |

(Continued)

FOREIGN PATENT DOCUMENTS

WO    WO-2017079782 A1 *  5/2017  ............. A61B 17/08

OTHER PUBLICATIONS

Online product information, including directions for use for Mepilex® at: https://www.molnlycke.us/products-solutions/mepilex/ and https://www.molnlycke.com/product-support/regulatory-support-and-product-information/ifu/.
(Continued)

*Primary Examiner* — Caitlin A Carreiro
(74) *Attorney, Agent, or Firm* — Trojan Law Offices (57) ABSTRACT

An improved adhesive bandage is disclosed. The adhesive bandage includes a rectangular portion of backing sheet material defining a forward and a rear side, pressure-sensitive adhesive on the forward side, separated by a rectangular portion of dressing material attached to a central area, and two rectangular portions of release paper each removably attached to either the forward or rear side of the adhesive bandage. The adhesive bandage also includes four tabs for the removal of the release paper, placed at the midpoints on either side of the adhesive bandage.

14 Claims, 8 Drawing Sheets

(51) Int. Cl.
*A61L 15/44* (2006.01)
*A61L 15/58* (2006.01)

(58) Field of Classification Search
USPC .... 602/41–44, 52, 54, 57, 58; 128/887–889; 206/440–441; 604/389–390
See application file for complete search history.

(56) References Cited

U.S. PATENT DOCUMENTS

| | | | |
|---|---|---|---|
| 5,722,943 A | | 3/1998 | Sessions |
| 5,840,052 A | * | 11/1998 | Johns .................... A61F 13/023 |
| | | | 602/54 |
| 8,822,751 B2 | * | 9/2014 | Gajiwala ............... A61F 15/001 |
| | | | 602/57 |
| 2013/0060184 A1 | * | 3/2013 | Rea ..................... A61F 13/0246 |
| | | | 602/54 |
| 2018/0353335 A1 | * | 12/2018 | Walker ................... A61B 17/08 |

OTHER PUBLICATIONS

Online directions for use for PolyMem® at: https://www.polymem.com/mkl/MKL009.pdf.
Online directions for use for 3M™ Tegaderm™ at: https://multimedia.3m.com/mws/media/2012650/framed-dressing-application-and-removal-instructions.pdf.

* cited by examiner

ADHESIVE BANDAGE

CROSS REFERENCES RELATED TO APPLICATION

Not applicable.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not applicable.

TECHNICAL FIELD

The technical field relates to the field medicine and more specifically relates to bandages and dressing for wound care.

BACKGROUND

The treatment of wounds, scrapes, and cuts typically involves the use of bandages with an exposed adhesive area for the purposes of creating a bond to the undamaged area of the skin, holding the bandage in place over the opening of the wound. The process of placing these conventional adhesive bandages presents various problems that diminish the effectiveness of the wound care. One of the drawbacks associated with the use of conventional adhesive bandages is that they are unwieldy to use, a characteristic that often leads to difficulties placing the adhesive bandage or misplacement thereof. Another drawback involves the amount of direct contact between the hands of the applicant of the bandage and either the adhesive portion of the bandage or the bandage itself. This contact creates various problems, most notably the transfer of unhealthy bacteria to the adhesive bandage and ultimately to the open wound. In certain cases, it may also cause the adhesive portion to lose some of its adhesive characteristics, resulting in the bandage not adequately adhering to the skin and thereby leaving the wound susceptible to further contamination. Other contamination issues arise with regards to the use of release paper, also known as release liner, on the adhesive bandages. The exposed nature of this aspect of the conventional adhesive bandage also leaves it vulnerable to being compromised by bacteria, again undesirably exposing the applicant's wound.

Due to the aforementioned shortcomings exhibited by the prior art, a need exists for improvements thereof, and particularly for an improved method of protecting the integrity of adhesive bandage devices used in the administration of wound care.

SUMMARY

An adhesive bandage is provided. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, the adhesive bandage includes a rectangular portion of backing sheet material defining a forward and a read side, pressure-sensitive adhesive deposited on the forward side of the backing sheet material, a rectangular portion of dressing material attached to a central area of the forward side of the backing sheet material such that the adhesive on the backing sheet material is exposed to the release paper on sides of the dressing material, a first rectangular portion of release paper removably attached to the forward side and rear side of the backing sheet material such that said first rectangular portion of release paper extends continuously from the midpoint of the dressing material to the left side of the dressing material and to the rear side of the backing sheet material, a first folded tab located at a midpoint of the dressing material on the first rectangular portion of the release paper, a second folded tab located at the midpoint of the rear side of the backing sheet material on the first rectangular portion of release paper, a second rectangular portion of release paper removably attached to the forward side and rear side of the backing sheet material such that said second rectangular portion of release paper extends continuously from the midpoint of the dressing material to the left side of the dressing material and to the rear side of the backing sheet material, a third folded tab located at midpoint of the dressing on the second rectangular portion of release paper, and a fourth folded tab located at midpoint of the rear side of the backing sheet material on the second rectangular portion of release paper.

BRIEF DESCRIPTION OF THE DRAWINGS

The accompanying drawings, which are incorporated in and constitute a part of this disclosure, illustrate various example embodiments. In the drawings.

DETAILED DESCRIPTION

The following detailed description refers to the accompanying drawings. Wherever possible, the same reference numbers are used in the drawings and the following description to refer to the same or similar elements. While embodiments may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the claimed subject matter. Instead, the proper scope of the claimed subject matter is defined by the appended claims.

The claimed subject matter improves over the prior art by providing a simple, easily applied adhesive bandage configured for self-application or application by a third-party. The claimed subject matter improves upon the effectiveness of wound care administered through the use of an adhesive bandage by reducing the contact between the dressing of the bandage and non-sterile surfaces, including the hands of the user. The claimed subject matter further improves over the prior art by providing disposable release paper that is handled while applying the bandage, as opposed to allowing handling of the bandage itself.

The claimed subject matter improves over the prior art by utilizing release paper, or liner paper, to cover all surfaces of the adhesive bandage. This enables a more controlled user experience and reduces or prevents any direct contact with the dressing material or backing material of the adhesive bandage. The claimed subject matter also includes four tabs, two on either side of the adhesive bandage, which further facilitates the appropriate use and placement of the bandage while reducing the frequency of contact between the applicator and sterile areas of the adhesive bandage, reducing incidents of infection. The claimed subject matter also protects the integrity of the adhesive portion of the bandage similarly through the placement of the release paper, which protects the adhesive portion thoroughly until it makes contact with the undamaged skin surrounding the wound site.

Figure 1:
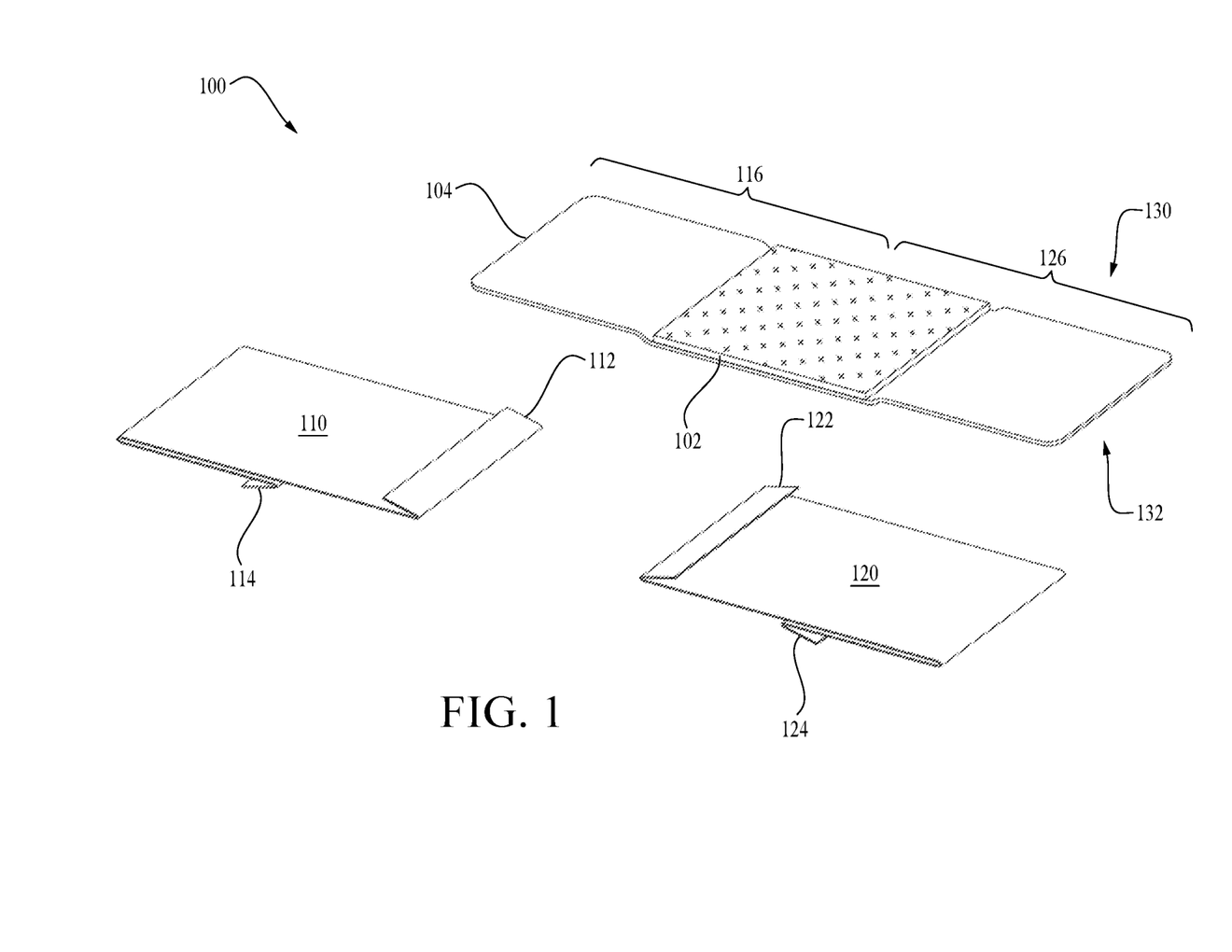
FIG. 1 is an exploded view of the adhesive bandage and the corresponding release paper, according to an example embodiment.
Figure 3:
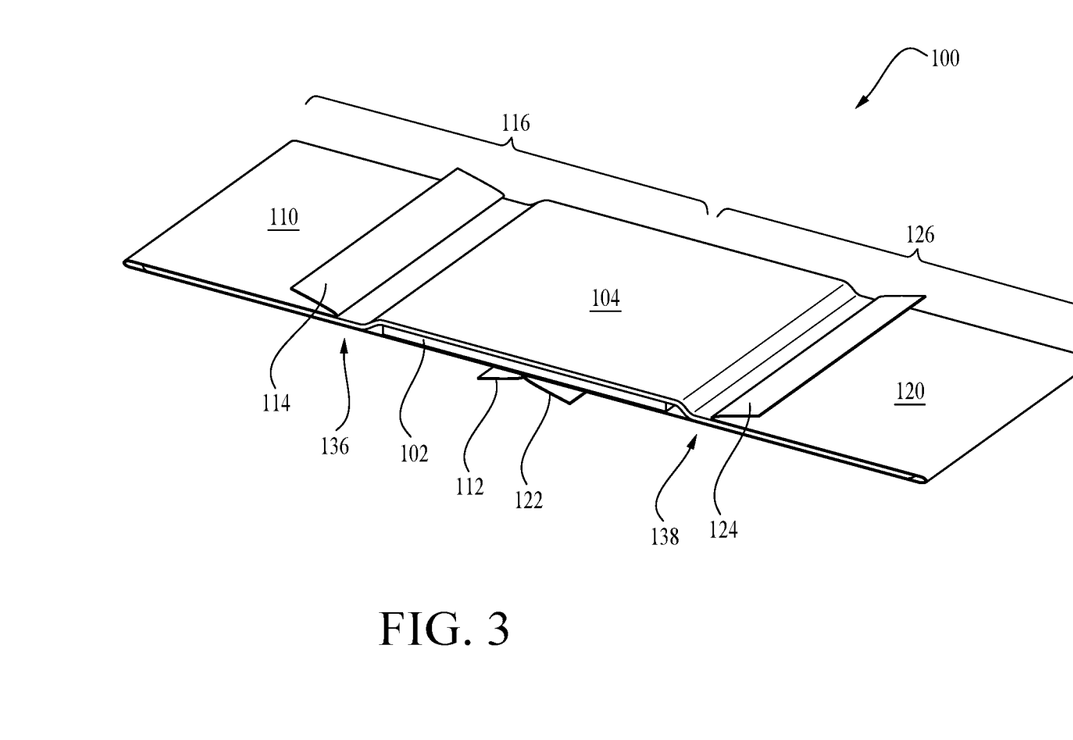
FIG. 3 is a reverse perspective view of FIG. 2 showing the adhesive bandage inside of its release paper according to the example embodiment of FIG. 1.

Referring now to the figures, FIG. 1 is a drawing illustrating an exploded view of the adhesive bandage 100, according to an example embodiment. FIG. 1 shows that the adhesive bandage 100 includes a rectangular backing sheet material 104, which defines an adhesive wound facing side 130 and a non-wound facing side 132 of the adhesive bandage 100. The rectangular backing sheet material 104 is divided into a first portion 116 and a second portion 126 with the dressing material 102 midway between them. In one embodiment, the rectangular backing sheet material 104 is coated on the adhesive wound facing side 130 with a pressure-sensitive adhesive on the first portion 116 and the second portion 126 on either side of the dressing material 102. The non-wound facing side 132 of the backing sheet material 104 not visible in FIG. 1, is shown in FIG. 3.

The backing sheet material 104 of the adhesive bandage 100 may be composed of any moisture permeable synthetic material. The backing sheet material 104 may also be composed of plastic, including polyethylene, polyurethane, or polyvinyl chloride. Another alternative material that may be used for the backing sheet material 104 is latex. The backing sheet material 104 may be a woven fabric material that is sufficiently breathable as to render it moisture permeable.

The dressing material 102 of the adhesive bandage 100 may be composed of foam or cotton, with the foam or cotton lined by a porous-polymer coating to prevent the dressing material 102 from adhering to a wound. The dressing material 102 may be sterile, or it may be antiseptic.

Figure 2:
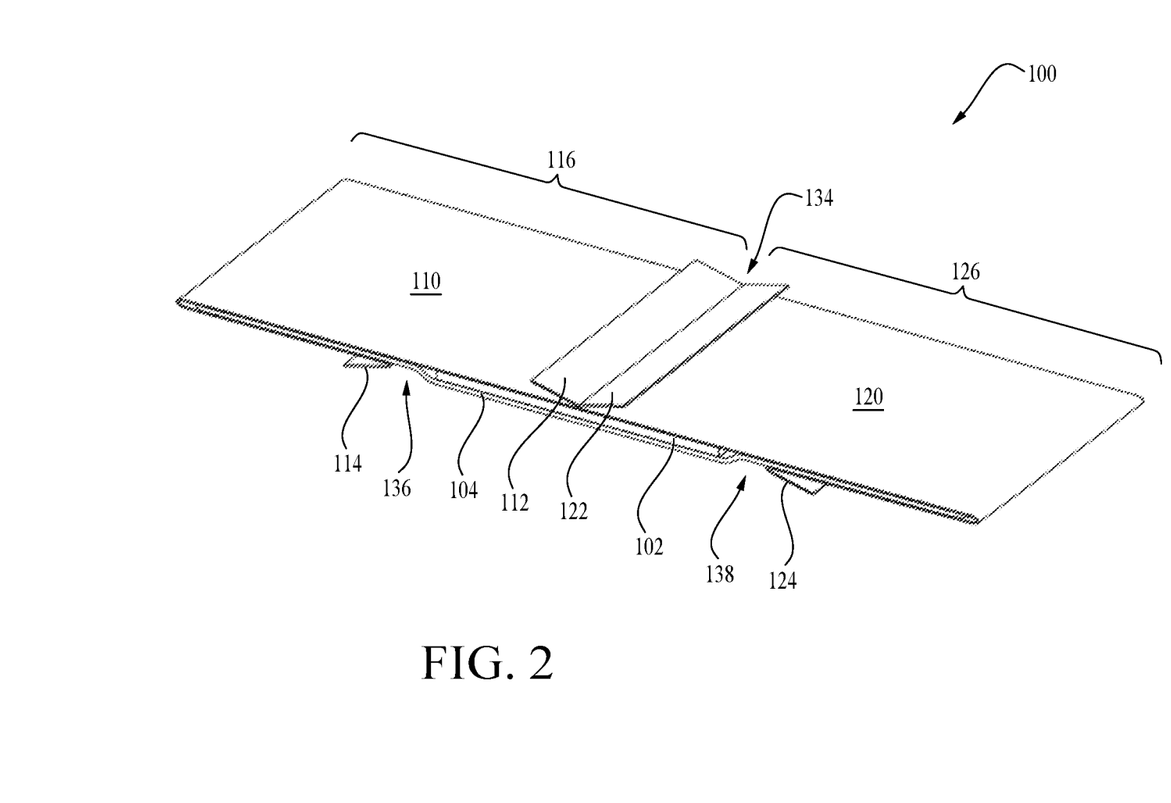
FIG. 2 is a perspective view of the adhesive bandage inside of its release paper according to the example embodiment of FIG. 1.

Still referring to FIG. 1, a first rectangular release paper 110 and a second rectangular release paper 120 are removably attached to the adhesive wound facing side 130 and non-wound facing side 132 of the adhesive bandage 100, such that they cover the dressing material 102. The first rectangular release paper 110 and the second rectangular release paper 120 are designed in a manner to produce four folded tabs: a first folded tab 112, a second folded tab 114, a third folded tab 122, and a fourth folded tab 124. In one embodiment, the four folded tabs, first folded tab 112, second folded tab 114, third folded tab 122, and fourth folded tab 124 may be folded backwards, as shown in FIG. 1-3. The first rectangular release paper 110 and the second rectangular release paper 120 may be composed of natural or synthetic paper, coated with a release agent. Alternatively, the first rectangular release paper 110 and second rectangular release paper 120 may be composed of a plastic liner. Folded tabs 112, 114, 122, and 124 are designed in such a way that they facilitate the application of the adhesive bandage 100 to a wound site 602 (FIG. 7) in a manner that significantly limits the potential for direct contact from nonsterile surfaces with the adhesive bandage 100. In various embodiments, the backing sheet material 104, dressing material 102, release paper 110 and 120 and folded tabs 112, 114, 122, and 124 may be rectangular, square, circular, triangular, or any other geometric shape.

FIG. 2 depicts the adhesive bandage 100 of FIG. 1, constructed to show the positioning of the first rectangular release paper 110 and second rectangular release paper 120. The first rectangular release paper 110 and second rectangular release paper 120 are designed to at least partially cover the backing sheet material 104 on both sides, as well as cover the dressing material 102. The first rectangular release paper 110 and second rectangular release paper 120 meet at the center line 134 of the adhesive wound facing side of the adhesive bandage 100, fully covering the adhesive wound facing side of the backing sheet material 104 as well as the dressing material 102. On the non-wound facing side of the adhesive bandage 100, the first rectangular release paper 110 and second rectangular release paper 120 extend to a first midpoint 136 and a second midpoint 138 of the first portion 116 and the second portion 126 of the backing sheet material 104, respectively, thereby embedding the dressing material 102. Note that first rectangular release paper 110 (like second rectangular release paper 120) is one continuous piece of paper that extends from the center line 134 of the adhesive wound facing side 130 of the adhesive bandage 100 around to the non-wound facing side of the adhesive bandage 100. FIG. 3 depicts the non-wound facing side of the adhesive bandage 100 of FIG. 2. FIG. 3 shows the first rectangular release paper 110 and second rectangular release paper 120 extending partially across the first portion 116 and the second portion 126 of the non-wound facing side 132 of the backing sheet material 104 where, on the adhesive wound facing side, the dressing material 102 is embedded. The second folded tab 114 is located at the first midpoint 136 of the first portion 116 of the non-wound facing side 132 of the backing sheet material 104 proximate to the dressing material 102. The fourth folded tab 124 is located at the second midpoint 138 of the second portion 126 of the non-wound facing side 132 of the backing sheet material 104 proximate to the dressing material 102.

Figure 4:
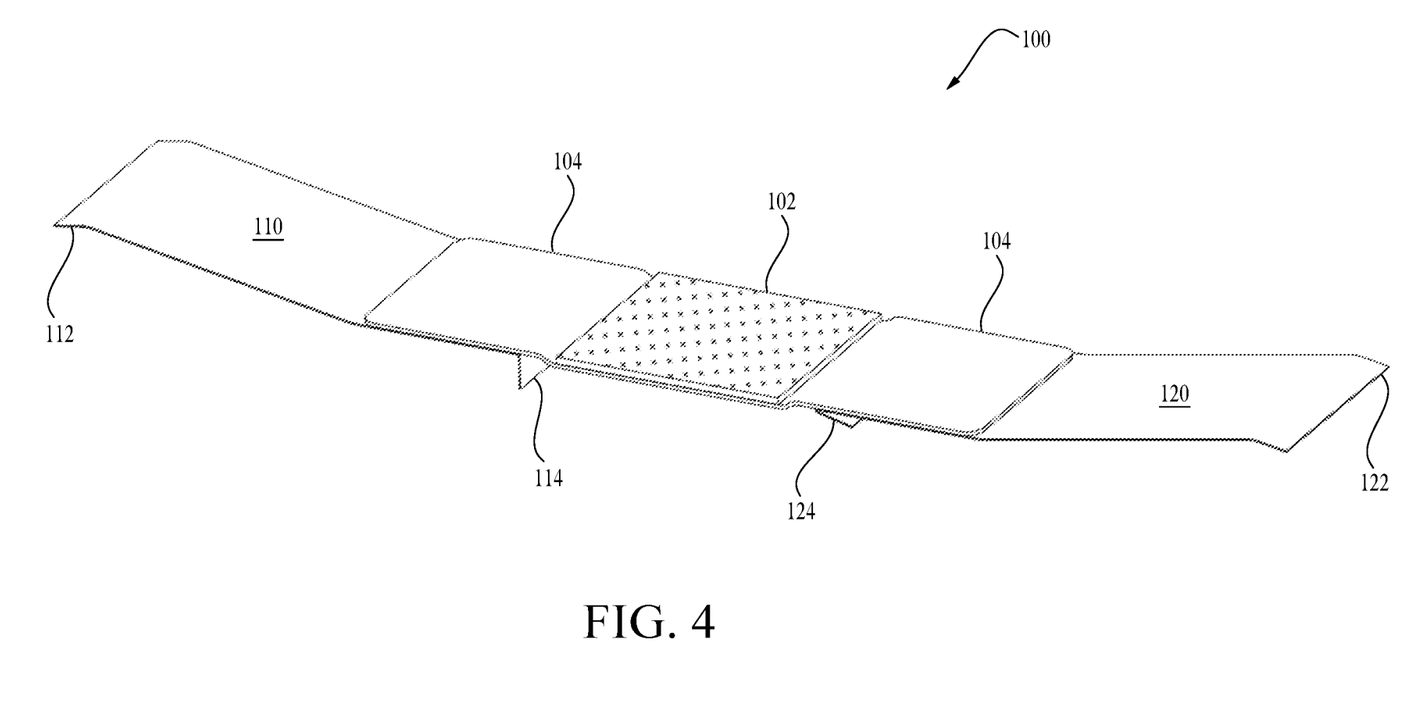
FIG. 4 is a perspective view of the adhesive bandage with its release paper removed from the adhesive surface, according to the example embodiment of FIG. 1.
Figure 6:
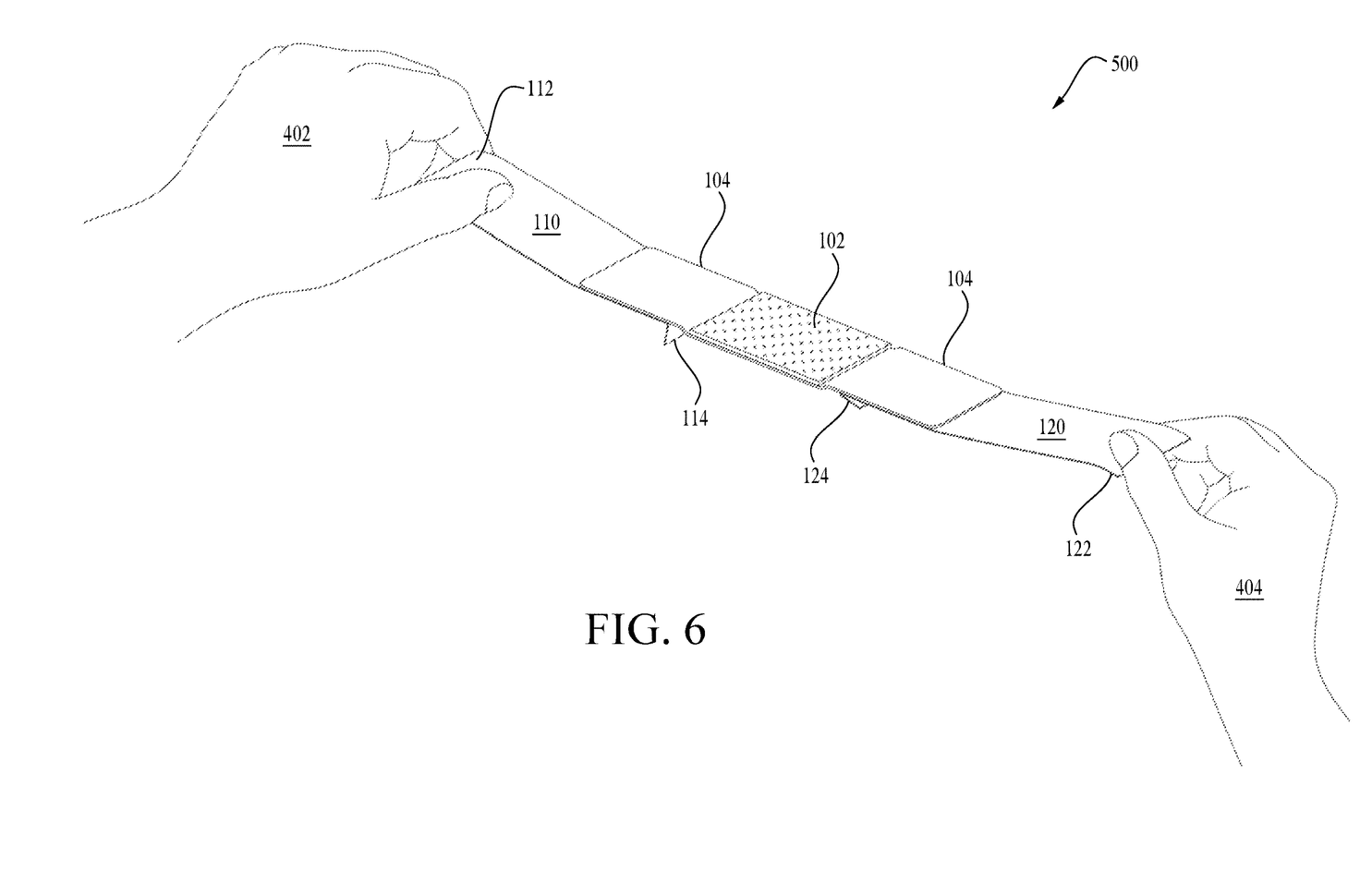
FIG. 6 illustrates the secondary stage of the application of the adhesive bandage, according to the example embodiment of FIG. 1.
Figure 7:
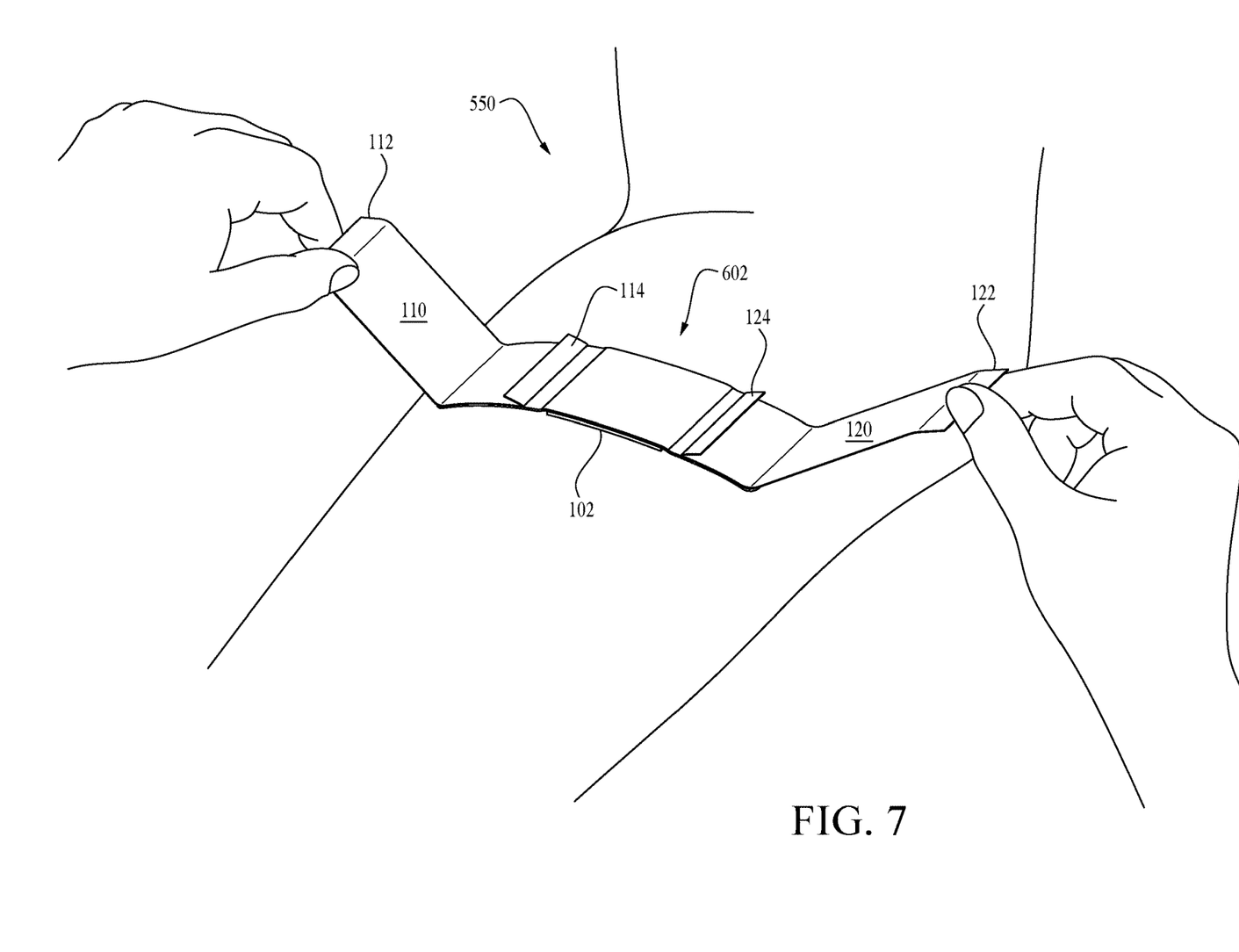
FIG. 7 illustrates the third stage of the application of the adhesive bandage, according to the example embodiment of FIG. 1.

FIG. 4 is a drawing depicting a perspective view of the adhesive bandage 100, showing the first rectangular release paper 110 and the second rectangular release paper 120 partially removed to expose the adhesive wound facing side 130 of the backing sheet material 104 and the dressing material 102, which the user will adhere to a wound site 602 (FIG. 7). FIG. 4 shows the adhesive bandage 100 after the first step 400 (FIG. 5) and second step 500 (FIG. 6) in applying the adhesive bandage 100 to a wound site 602, i.e., opening the adhesive bandage 100 and exposing the dressing material 102 for application to the wound site 602. Note that in both the first step 400 and second step 500, it is not necessary that any portion of the adhesive bandage 100, other than the release papers 110 and 120, is touched by the person applying the adhesive bandage 100.

Figure 5:
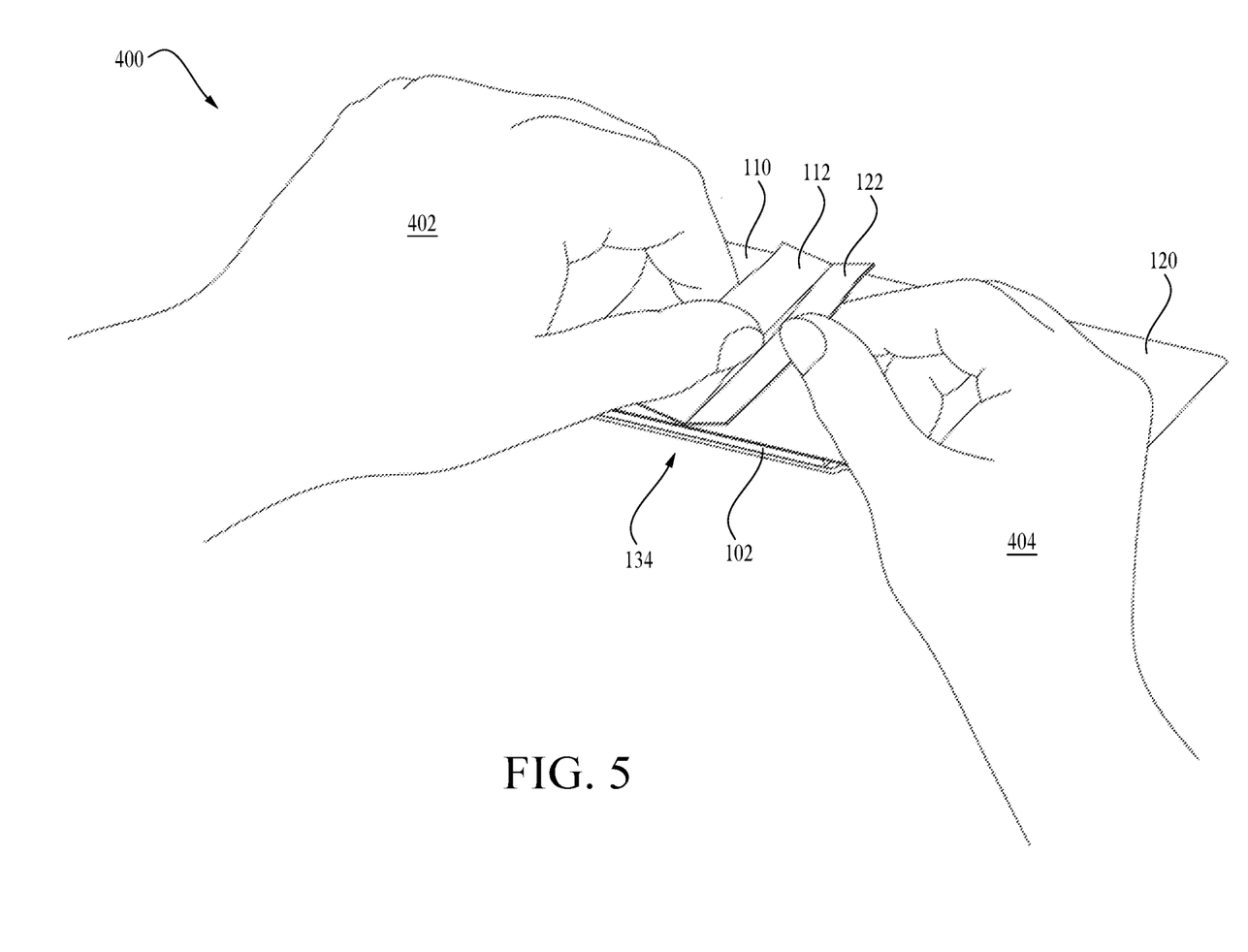
FIG. 5 illustrates the initial stage of the application of the adhesive bandage, according to the example embodiment of FIG. 1.

FIG. 5 is a drawing illustrating the first step 400 of the application process when applying the adhesive bandage 100. The left hand, or first hand 402 of the user is shown pinching the first folded tab 112 of the first portion 116 of release paper 110. Similarly, the right hand, or second hand 404 is shown pinching the third folded tab 122 on the second rectangular portion of release paper 120. The user is now ready to pull on folded tabs 112 and 122 to the position shown in FIG. 6. Note that in the first step, no portion of the adhesive bandage 100, other than the release papers 110 and 120, was touched by the person applying the adhesive bandage 100.

Figure 8:
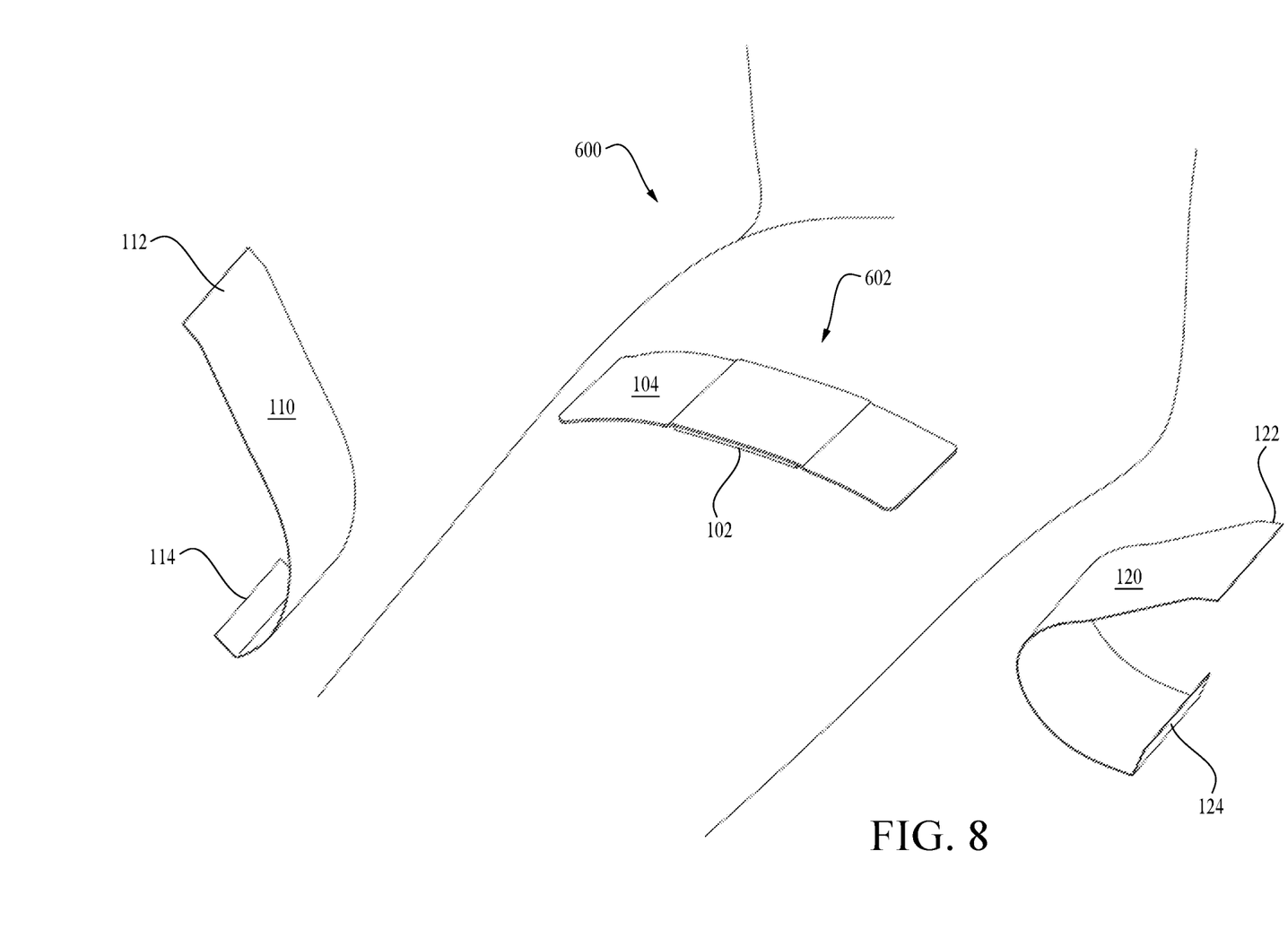
FIG. 8 illustrates the final stage of the application of the adhesive bandage, according to the example embodiment of FIG. 1.

FIG. 6 is a drawing illustrating the second step 500 of the application process when applying the adhesive bandage 100. In FIG. 6, the user is shown using the first hand 402 and the second hand 404 to separate the adhesive wound facing side 130 of the first rectangular release paper 110 and second rectangular release paper 120 in an outward direction, exposing the adhesive wound facing side of the backing sheet material 104, thereby facilitating the placement of the adhesive bandage 100 over the wound site 602 as shown in FIGS. 7-8. In this step, the person applying the adhesive bandage 100 may pull outwardly on the release first rectangular release paper 110 and second rectangular release paper 120 to stretch the adhesive bandage 100 before application to the wound site 602. Note that in the second step, no portion of the adhesive bandage 100, other than the release papers 110 and 120, was touched by the person applying the adhesive bandage 100.

FIG. 7 shows the intermediary stage, or third step 550, between the removal of the first rectangular release paper 110 and second rectangular release paper 120 from the adhesive bandage 100 shown in FIG. 6 and the final step 600 shown in FIG. 8. FIG. 8 is a drawing showing the final step 600 of the application process when applying the adhesive bandage 100. In FIG. 8 the adhesive bandage 100 has been placed to cover the wound site 602, with the adhesive wound facing side of the backing sheet material 104, which contains the pressure sensitive adhesive in contact with the undamaged skin, and the dressing material 102 over the wound. FIG. 8 further shows the first rectangular release paper 110 and the second rectangular release paper 120 fully removed from the adhesive bandage 100. Note that in the third step 550 and final step 600, no portion of the adhesive bandage 100, other than the first rectangular release paper 110 and the second rectangular release paper 120, was touched by the person applying the adhesive bandage 100.

What is claimed is:

1. An adhesive bandage for application on a wound comprising:
   (a) a rectangular portion of backing sheet material defining a wound-facing forward side and a rear side, the backing sheet material having a first end and a second end, the backing sheet material composed of a moisture permeable material;
   (b) a pressure-sensitive adhesive deposited on the forward side of the backing sheet material;
   (c) a rectangular portion of dressing material attached to a central area of the forward side of the backing sheet material between the first end and the second end, wherein the dressing material is cotton lined with a porous-polymer coating;
   (d) a first rectangular portion of release paper removably and directly attached to the forward side and rear side of the first end such that said first rectangular portion of release paper extends continuously from a midpoint of the dressing material around to the rear side of the first end, the first rectangular portion of release paper configured to separate entirely from the forward side while remaining directly attached to the rear side of the first end;
   (e) a first folded tab on the first rectangular portion of release paper, the first folded tab located at the midpoint of the dressing material;
   (f) a second folded tab on the first rectangular portion of release paper, the second folded tab located on the rear side of the first end for removing the first rectangular portion of release paper from the backing sheet material;
   (g) a second rectangular portion of release paper removably and directly attached to the forward side and rear side of the second end such that said second rectangular portion of release paper extends continuously from the midpoint of the dressing material around to the rear side of the second end, the second rectangular portion of release paper configured to separate entirely from the forward side while remaining directly attached to the rear side of the second end;
   (h) a third folded tab on the second rectangular portion of release paper, the third folded tab located at the midpoint of the dressing material;
   (i) a fourth folded tab on the second rectangular portion of release paper, the fourth folded tab located on the rear side of the second end for removing the second rectangular portion of release paper from the backing sheet material.

2. The adhesive bandage as recited in claim 1, wherein the backing sheet material is a woven fabric material sufficiently breathable as to render it moisture permeable.

3. The adhesive bandage as recited in claim 1, wherein the dressing material has been sterilized and/or is antiseptic.

4. The adhesive bandage as recited in claim 1, wherein the first, second, third, and fourth folded tabs are folded backwards, towards their respective release papers to reduce direct contact with the backing sheet material, dressing material, and adhesive.

5. An adhesive bandage for a dressing a wound, the bandage comprising:
   (a) a portion of backing sheet material defining a wound-facing forward side and a rear side having a first end and a second end;
   (b) a pressure-sensitive adhesive deposited on the forward side of the backing sheet material;
   (c) a portion of dressing material attached to a central area of the forward side of the backing sheet material between the first end and the second end;
   (d) a first portion of release paper removably and directly attached to said forward side and said rear side of the first end such that said first portion of release paper extends continuously from the dressing material around the first end, the first portion of release paper configured to separate entirely from the forward side while remaining directly attached to the rear side of the first end;
   (e) a second portion of release paper removably and directly attached to the forward side and the rear side of the second end such that said second portion of release paper extends continuously from the dressing material around the second end, the second portion of release paper configured to separate entirely from the forward side while remaining directly attached to the rear side of the second end; and wherein the first portion of release paper and the second portion of release paper are configured to be removed from the backing sheet material once the dressing material and backing sheet material are affixed to the wound.

6. The adhesive bandage as recited in claim 5, further comprising a first folded tab on the first portion of release paper, the first folded tab located at a midpoint of the dressing material, and a second folded tab on the first portion of release paper, the second folded tab located on the rear side of the first end.

7. The adhesive bandage as recited in claim 6, further comprising a third folded tab on the second portion of release paper, the third folded tab located at a midpoint of the dressing material, and a fourth folded tab on the second portion of release paper, the fourth folded tab located on the rear side of the second end.

8. The adhesive bandage as recited in claim 7, wherein the first, second, third, and fourth folded tabs are each folded backwards, towards their respective release papers to reduce direct contact with the backing sheet material, dressing material, and adhesive.

9. The adhesive bandage as recited in claim 5, wherein the backing sheet material is a woven fabric material sufficiently breathable as to render it moisture permeable.

10. The adhesive bandage as recited in claim 5, wherein the dressing material has been sterilized and/or is antiseptic.

11. The adhesive bandage as recited in claim 5, wherein the portion of backing sheet material is rectangular, square, circular, triangular, or any other geometric shape.

12. The adhesive bandage as recited in claim 5, wherein the portion of dressing material is rectangular, square, circular, triangular, or any other geometric shape.

13. The adhesive bandage as recited in claim 5, wherein the first portion of release paper is rectangular, square, circular, triangular, or any other geometric shape.

14. The adhesive bandage as recited in claim 5, wherein the second portion of release paper is rectangular, square, circular, triangular, or any other geometric shape.

* * * * *